(12) United States Patent
Gellman et al.

(10) Patent No.: US 8,382,771 B2
(45) Date of Patent: Feb. 26, 2013

(54) RADIAL COIL EXPANDABLE MEDICAL WIRE

(75) Inventors: Barry N. Gellman, N. Easton, MA (US); Benjamin J. Bottcher, Franklin, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 181 days.

(21) Appl. No.: 12/631,402

(22) Filed: Dec. 4, 2009

(65) Prior Publication Data
US 2010/0082059 A1  Apr. 1, 2010

Related U.S. Application Data

(63) Continuation of application No. 10/116,828, filed on Apr. 5, 2002, now abandoned.

(51) Int. Cl.
*A61B 17/22* (2006.01)
*A61B 17/26* (2006.01)

(52) U.S. Cl. .......... 606/127; 606/113; 606/114

(58) Field of Classification Search .......... 606/127, 606/198, 200, 113, 114
See application file for complete search history.

(56) References Cited

U.S. PATENT DOCUMENTS

| | | | |
|---|---|---|---|
| 2,756,752 A | 7/1956 | Scherlis | |
| 4,003,369 A | 1/1977 | Heilman et al. | |
| 4,080,706 A | 3/1978 | Heilman et al. | |
| 4,543,090 A * | 9/1985 | McCoy | 604/95.05 |
| 4,706,671 A | 11/1987 | Weinrib | |
| 4,724,846 A | 2/1988 | Evans, III | |
| 4,813,925 A | 3/1989 | Anderson et al. | |
| 4,957,479 A | 9/1990 | Roemer | |
| 5,054,501 A | 10/1991 | Chuttani et al. | |
| 5,122,154 A | 6/1992 | Rhodes | |
| 5,499,973 A * | 3/1996 | Saab | 604/96.01 |
| 5,514,176 A | 5/1996 | Bosley, Jr. | |
| 5,536,274 A | 7/1996 | Neuss | |
| 5,562,641 A | 10/1996 | Flomenblit et al. | |
| 5,609,605 A | 3/1997 | Marshall et al. | |
| 5,647,843 A | 7/1997 | Mesrobian et al. | |
| 5,681,274 A | 10/1997 | Perkins et al. | |
| 5,795,319 A | 8/1998 | Ali | |
| 5,843,176 A | 12/1998 | Weier | |
| 5,962,007 A | 10/1999 | Cooper | |
| 5,964,744 A | 10/1999 | Balbierz et al. | |
| 6,019,779 A | 2/2000 | Thorud et al. | |
| 6,027,516 A | 2/2000 | Kolobow et al. | |
| 6,093,199 A | 7/2000 | Brown et al. | |
| 6,113,621 A | 9/2000 | Wiktor | |
| 6,149,574 A * | 11/2000 | Trauthen et al. | 600/3 |
| 6,174,305 B1 | 1/2001 | Mikus et al. | |

(Continued)

FOREIGN PATENT DOCUMENTS

| | | |
|---|---|---|
| EP | 1064888 A1 | 3/2001 |
| EP | 1208816 A2 | 5/2002 |

(Continued)

*Primary Examiner* — Tuan V Nguyen
(74) *Attorney, Agent, or Firm* — Bookoff McAndrews, PLLC (57) ABSTRACT

An expandable medical wire can be used to entrain biological or foreign material during a medical procedure, such as lithotripsy. The wire also can be used to remove the material safely from the body. Generally, the wire includes a sleeve and a core, where the sleeve, the core, or both include a portion or portions that can be deployed to form an expanded coiled configuration. The expanded coiled configuration can be collapsed to facilitate positioning the wire within an anatomical lumen. In addition, the wire can be used as a conventional guide wire or as a self-anchoring guide wire.

24 Claims, 9 Drawing Sheets

U.S. PATENT DOCUMENTS

| | | |
|---|---|---|
| 6,214,042 B1 | 4/2001 | Jacobsen et al. |
| 6,258,098 B1 | 7/2001 | Taylor et al. |
| 6,290,721 B1 | 9/2001 | Heath |
| 6,368,328 B1 | 4/2002 | Chu et al. |
| 6,620,172 B1 | 9/2003 | Dretler et al. |
| 6,740,096 B2 | 5/2004 | Teague et al. |
| 6,740,273 B2 * | 5/2004 | Lee ............... 264/130 |
| 6,932,830 B2 * | 8/2005 | Ungs ............... 606/200 |
| 7,285,126 B2 | 10/2007 | Sepetka et al. |
| 7,338,501 B2 | 3/2008 | Teague et al. |
| 2001/0031971 A1 | 10/2001 | Dretler et al. |
| 2001/0031980 A1 | 10/2001 | Wensel et al. |

FOREIGN PATENT DOCUMENTS

| | | |
|---|---|---|
| WO | WO94/06357 | 3/1994 |
| WO | WO97/27808 | 8/1997 |
| WO | WO98/25656 | 6/1998 |
| WO | WO99/23958 | 5/1999 |
| WO | WO01/01869 | 1/2001 |

* cited by examiner

RADIAL COIL EXPANDABLE MEDICAL WIRE

This is a continuation of application Ser. No. 10/116,828, filed Apr. 5, 2002 now abandoned, which is incorporated herein by reference.

TECHNICAL FIELD

The invention generally relates to deployable medical devices for insertion into anatomical lumens.

BACKGROUND INFORMATION

Blockages and obstructions can develop in certain areas of the body, such as in the kidneys, pancreas, esophagus, and gallbladder. Minimally invasive medical procedures generally cause limited trauma to the tissue of a patient and can be used to eliminate problematic obstructions. Lithotripsy and ureteroscopy, for example, are used to treat urinary calculi, e.g., kidney stones, in the ureter of patients.

Lithotripsy is a medical procedure that uses energy in various forms, such as acoustic or electrical shock waves, pneumatic or hydraulic pulsation, or laser beams, to break up biological concretions, such as urinary calculi. The force of the energy, when applied either extracorporeally or intracorporeally, usually in focused and continuous or successive bursts, comminutes a kidney stone into smaller fragments that may be extracted from the body or allowed to pass through urination. With the help of imaging tools, such as transureteroscopic video technology and fluoroscopic imaging, the operator of the lithotripter device can monitor the progress of the medical procedure and terminate treatment when residual fragments are small enough to be voided or removed. Examples of such obstructions and the effects of treatment can be found in the published patent application US 2001/0031971, the disclosure of which is incorporated by reference herein in its entirety.

Intracorporeal fragmentation of urinary calculi can prove problematic, because stones and/or stone fragments in the ureter may become repositioned closer to and possibly migrate back toward the kidney, thereby requiring further medical intervention to prevent aggravation of the patient's condition.

Many known stone extraction devices are rigid and lack the maneuverability and flexibility to engage and disengage repeatedly a stone without harming the surrounding tissue. For example, if a stone is still too large to be extracted without further fragmentation, it can be difficult to disengage the stone from such an extraction device without damaging the delicate lining of the ureteral wall.

SUMMARY OF THE INVENTION

The invention generally relates to preventing migration of material during a medical procedure, and to safely and efficiently ensnaring and extracting material from a body. It is desirable to be able to extract such material from the body using a single instrument, which prevents the need for successive instrumentation. A medical device according to the invention can be used to repeatedly ensnare and extract or sweep material (such as stones, stone fragments, and other biological and/or foreign material) while minimizing trauma to surrounding tissue. Accordingly, the device can be deployed and collapsed repeatedly, as and when required during the medical procedure.

In one aspect, the invention is directed to a medical device including an elongate core and an elongate sleeve. The sleeve includes a lumen that extends longitudinally within at least a portion of the elongate sleeve. The core is slidably disposable within the lumen of the sleeve. The sleeve also includes a plurality of coils that are configured in a conical shape when the core is removed from a section of the lumen extending through the plurality of coils. The sleeve assumes a substantially linear configuration when the core is inserted within the section of the lumen extending through the plurality of coils.

The conical shape formed by the plurality of coils can be used to ensnare objects in an anatomical lumen. When the sleeve is in the substantially linear configuration, a portion of the sleeve can be advanced beyond an object in an anatomical lumen. The coils can then be allowed to assume their conical shape by removing the slidable core to form a structure capable of ensnaring objects in the anatomical lumen. The core can be extended back through the lumen of the sleeve to return the sleeve into the substantially linear configuration for repositioning the device in the anatomical lumen. The conical shape can then be redeployed by retracting the core from the section of the lumen extending through the plurality of coils. Thus, reversible transformation of the coiled and linear configurations of the sleeve can facilitate repeated positioning and deployment of the medical device in appropriate locations in an anatomical lumen.

In one embodiment of the invention, the plurality of coils forming a conical shape are located a predetermined distance from a proximal end of the sleeve. In another embodiment, the sleeve further includes at least one coiled element located in a portion of the sleeve distal to the plurality of coils. The at least one coiled element forms when the core is removed from a section of the lumen extending through the at least one coiled element and assumes a substantially linear configuration when the core is inserted into the section of the lumen extending through the at least one coiled element. The at least one coiled element can be used for anchoring the medical device and the conical shape can be used for ensnaring objects in the anatomical lumen.

In another aspect, the invention is directed to a medical device including an elongate sleeve and an elongate core. The elongate sleeve includes a first portion and a second portion that is more rigid than the first portion and a lumen that extends longitudinally within at least a portion of the elongate sleeve. The core is slidably disposable within the lumen and includes a section that changes shape when disposed within the first portion of the sleeve causing an outer diameter of the sleeve to increase. The core is retained in a substantially linear configuration when the section that changes shape is disposed in the second portion of the sleeve.

The first portion and the second more rigid portion of the sleeve can have different wall thicknesses. In one embodiment, the first portion of the sleeve has a wall thickness substantially less than the wall thickness of the second portion of the sleeve. In another embodiment, the first portion includes an expandable balloon. In yet another embodiment, the section that changes shape forms a coiled configuration when disposed in the first portion.

In yet another aspect, the invention is directed to a medical device that includes an elongate sleeve and an elongate core. The sleeve includes a lumen that extends longitudinally within at least a portion of the elongate sleeve and a sleeve section that changes shape. The elongate core is slidably disposable within the lumen of the sleeve and includes a core section that changes shape. Each of the sleeve and core sections retain a substantially linear configuration when restrained and form a substantially coiled configuration when aligned. The sleeve and core sections form a substantially coiled configuration when unrestrained.

In one embodiment, the coiled configuration of both the sleeve and the core can be substantially equal in shape and size. In another embodiment, each of the sleeve and core sections are adapted to remain in the coiled configuration when at least partially aligned. In yet another embodiment, each of the sleeve and core sections retain the substantially linear configuration when at least partially misaligned.

In various embodiments of the two foregoing aspects of the invention, the sections that change shape can include at least one coil. The sections that change shape can also include a plurality of coils that form different shapes, such as conical, spherical, helical, frusto-conical, or combinations thereof. In a particular embodiment, the shape formed by the plurality of coils is a generally conical shape.

In all the foregoing aspects of the invention, the core and the sleeve can be made from the same or different materials. In one embodiment, the sleeve includes a shape-memory material. In another embodiment, the core includes a shape-memory material. In yet another embodiment, both the sleeve and the core include a shape-memory material. Shape-memory materials are materials that can be formed into a particular shape, retain that shape during resting conditions, (e.g., when little or no external forces are applied to the shape), be deformed into a second shape upon subjecting the initial shape to a sufficiently high external force, and revert back to substantially the initial shape once the external forces are removed or at least lessened. Examples of shape-memory materials include synthetic plastics, stainless steel, and superelastic, metallic alloys, such as nickel/titanium (commonly referred to as nitinol), copper, cobalt, vanadium, chromium, and iron.

In addition, the sleeve and the core can have essentially any cross-sectional shape, such as polygonal, arcuate, or combinations of polygonal and arcuate elements. In the present application, the term polygonal is used to denote any shape including at least two line segments, such as rectangles, trapezoids, and triangles. Examples of arcuate shapes include circular and elliptical. Further, the sleeve can include a coating disposed on an external surface of the sleeve. The coating can be a polymeric material, for example, polytetraflouroethylene, expanded polytetraflouroethylene, ethylene-tetrafluoroethylene, and silicone. The coating can cover a substantial portion of the external surface of the sleeve.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DESCRIPTION

Embodiments of the present invention are described below. The invention is not limited to these embodiments, and various modifications to the disclosed embodiments are also encompassed by the invention. A medical device according to the invention can be used to entrain biological and/or foreign material during a medical procedure. The medical procedure can involve the fragmentation of the material. The device can also be used to remove the material and/or fragments of the material safely from the body. In addition, the device can be used as a self-anchoring guide wire.

Figure 1A:
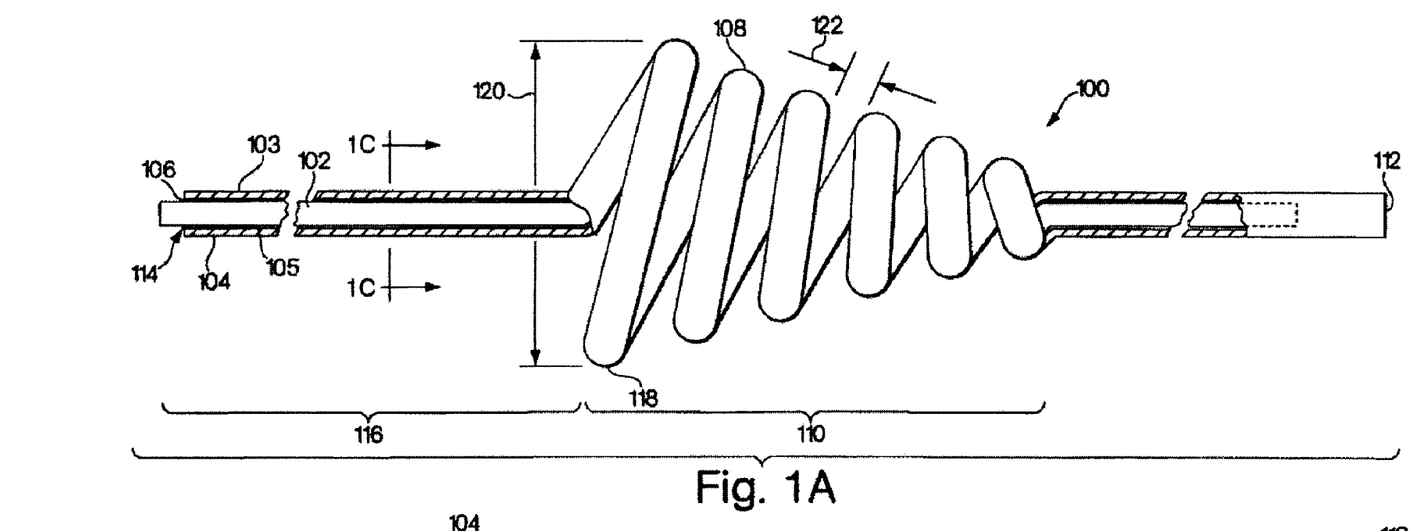
FIG. 1A is a partially sectioned schematic view of one embodiment of a medical device in accordance with the invention.
Figures 1B, 1C:
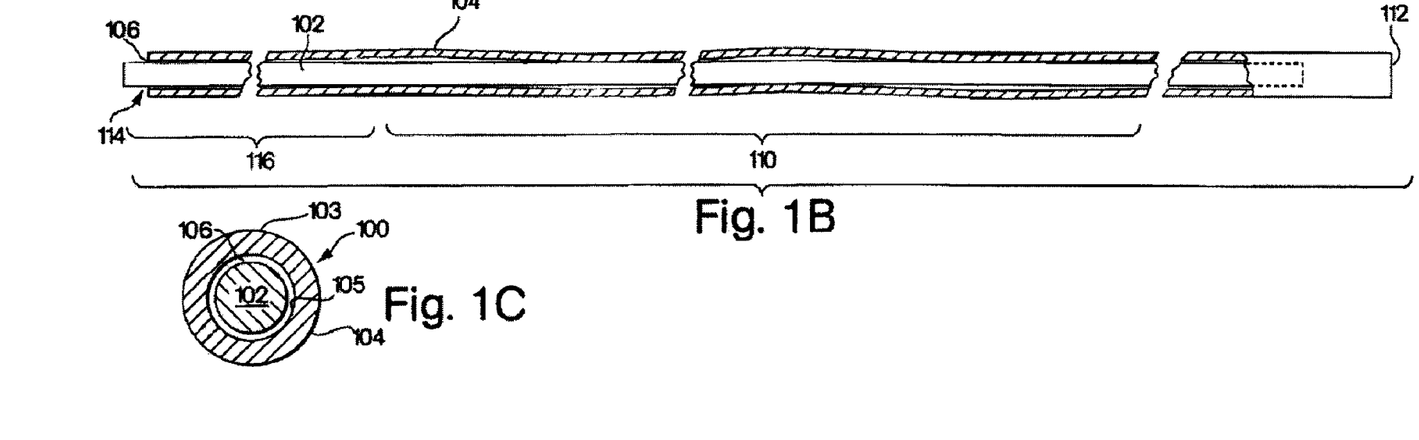
FIG. 1B is another partially sectioned schematic view of the medical device of FIG. 1A, with a sleeve in a substantially linear configuration.
FIG. 1C is a cross-sectional view of the medical device of FIG. 1A taken at line 1C-1C.

FIGS. 1A and 1B depict a medical device 100 in accordance with the invention in two different configurations. The medical device 100 includes an elongate sleeve 104 and an elongate core 102. The sleeve 104 includes a lumen 106 that extends longitudinally within at least a portion of the sleeve 104, a distal end 112, and a proximal end 114. In one embodiment the sleeve includes an outer wall 103 and an inner wall 105. The core 102 is adapted to be disposed within the lumen 106 of the sleeve 104. At least a portion 110 of the sleeve 104 is adapted to form a plurality of coils 108 disposed in a conical shape when the core 102 is removed from a section of the lumen 106 that extends through the plurality of coils 108 (FIG. 1A). The plurality of coils 108 are straightened and the sleeve 104 assumes a substantially linear configuration when the core 102 is inserted within the section of the lumen 106 extending through the plurality of coils 108 (FIG. 1B). The proximal end 118 of the plurality of coils 108 is located a predetermined distance 116 from the proximal end 114 of the sleeve. The medical device 100 is configured to support the treatment and/or removal of foreign objects and organic material, e.g., blood clots, tissue, and biological obstructions, such as urinary, biliary, and pancreatic stones, from an anatomical lumen.

The sleeve 104 is constructed, at least in part, of a shape-memory material that enables the sleeve 104 to assume a coiled configuration forming a conical shape when the core 102 is removed from the section of the lumen 106 extending through the plurality of coils 108. The shape-memory material of the sleeve 106 also enables the plurality of coils 108 to assume a substantially linear configuration when the core 102 is extended through the section of the lumen 106 extending through the plurality of coils 108, as shown in FIG. 1B, without significantly affecting the ability of the sleeve 104 to revert back into the coiled configuration when the core 102 is removed from the section of the lumen 106 extending through the plurality of coils 108.

Shape-memory materials suitable for use in forming the sleeve 104 include plastics, stainless steel, and metallic alloys of nickel, titanium, cooper, cobalt, vanadium, chromium, and iron. In one embodiment, the shape-memory material forming the sleeve 104 is a superelastic material, such as nitinol, which is a nickel-titanium alloy. The core 102 can also be made from a shape-memory material, such as nitinol. Other suitable materials for the manufacture of the sleeve or the core include: thermoplastic polyurethane (TPU), thermoplastic polyester elastomers, nylons, and equivalent materials. Additional suitable materials will be apparent to those skilled in the art.

FIG. 1C is a cross-sectional view of the medical device 100 of FIGS. 1A and 1B. In the embodiment shown, the medical device 100 has a generally circular cross-section; however, the cross-section could be polygonal, arcuate, or combinations of arcuate and polygonal elements. FIG. 1C depicts the core 102 disposed within the lumen 106 of the sleeve 104. In one embodiment, the sleeve includes an outer wall 103 and an inner wall 105.

Figure 2A:
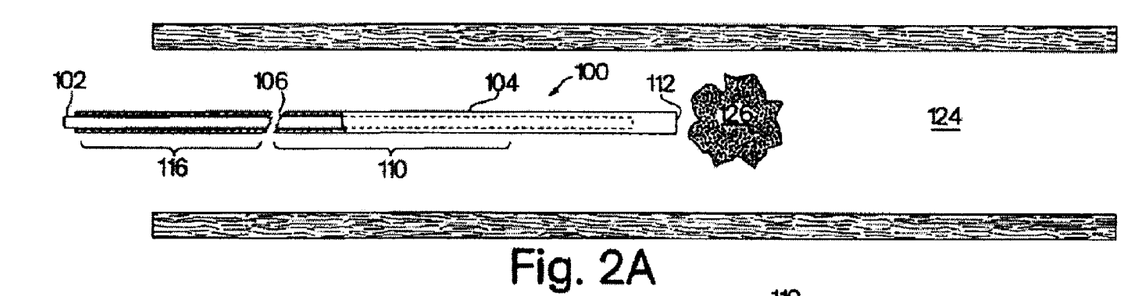
FIG. 2A is a cross-sectional schematic view of the medical device of FIG. 1A with the invention positioned inside the anatomical lumen.
Figure 2B:
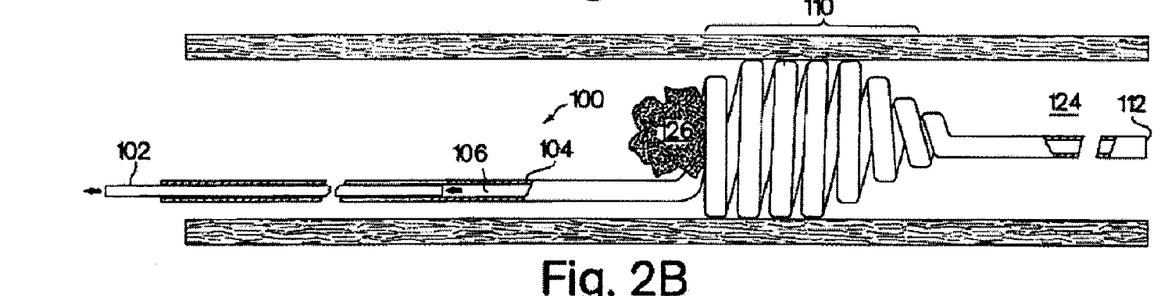
FIG. 2B is a partially sectioned schematic view of the medical device of FIG. 2A deployed within the anatomical lumen.
Figure 2C:
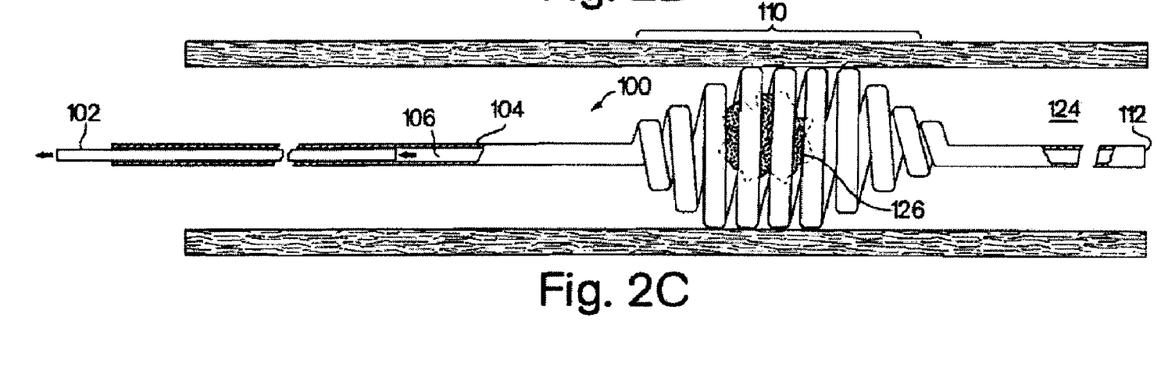
FIG. 2C is another partially sectioned schematic view of the medical device of FIG. 2A deployed within the anatomical lumen.

FIGS. 2A-2C depict a medical device 100, positioned within an anatomical lumen 124 of a patient. The plurality of coils serve as a physical barrier or backstop during the lithotripsy procedure to ensure that the smaller fragments do not migrate in an undesired direction, e.g., back toward the kidney. The instrumentation used to perform the lithotripsy can be introduced into the desired location adjacent to the obstruction via another catheter or guide wire.

In one aspect, a health care practitioner inserts the medical device 100 within an anatomical lumen 124, such as a ureteral passage, to ensnare fragments of stones resulting from a lithotripsy procedure or other objects obstructing the lumen. In this aspect, the plurality of coils 108 is deployed into a conical shape within the anatomical lumen 124 by retracting the core 102 from within the lumen 106 of the sleeve 104, as depicted in FIG. 2B. The medical device 100 can be inserted into an anatomical lumen 124 of a patient via a catheter or a guide wire. In one method of use of the medical device 100, a health care practitioner inserts the medical device 100 into an anatomical lumen 124 with the sleeve 104 in a substantially linear configuration and the core 102 extended through the section of the lumen 106 that extends through the plurality of coils 108, as shown in FIG. 2A. For example, in a lithotripsy procedure to remove a kidney stone from a patient's ureter, the medical device 100 is introduced into the patient's urinary passage until the distal end 112 passes beyond the location of the stone 126 lodged in the ureter. The health care practitioner then deploys the plurality of coils 108 downstream of the stone 126 by retracting the core 102 from the section of the lumen 106 extending through the plurality of coils 108, as depicted in FIG. 2B. The plurality of coils 108 act as a backstop to prevent the migration of the fragments, as shown in FIG. 2B. The maximum outside diameter 120 of the plurality of coils 108 is designed to be substantially the same as or slightly greater than the inside diameter of the anatomical lumen 124 so that the passage will be sufficiently occluded to prevent any subsequent migration of the kidney stone 126.

Once the lithotripsy procedure is complete, the health care practitioner can extend the core 102 through the section of the lumen 106 that extends through the plurality of coils 108 in order to straighten, reposition and redeploy the plurality of coils to ensnare the fragments, as shown in FIG. 2C. If the fragments are small enough to pass through the anatomical lumen, the health care practitioner can drag the fragments from the anatomical lumen and out of the body. If, however, the fragments of the stone are still too large to pass through sections of the anatomical lumen, the sleeve 104 can be straightened by extending the core 102 through the section of the lumen 106 that extends through the plurality of coils 108. In this scenario, the health care practitioner can repeat the treatment procedure by repositioning and redeploying the plurality of coils 108 beyond the stone 126 and performing a second lithotripsy procedure to further fragment the remaining obstructions.

Figure 3A:
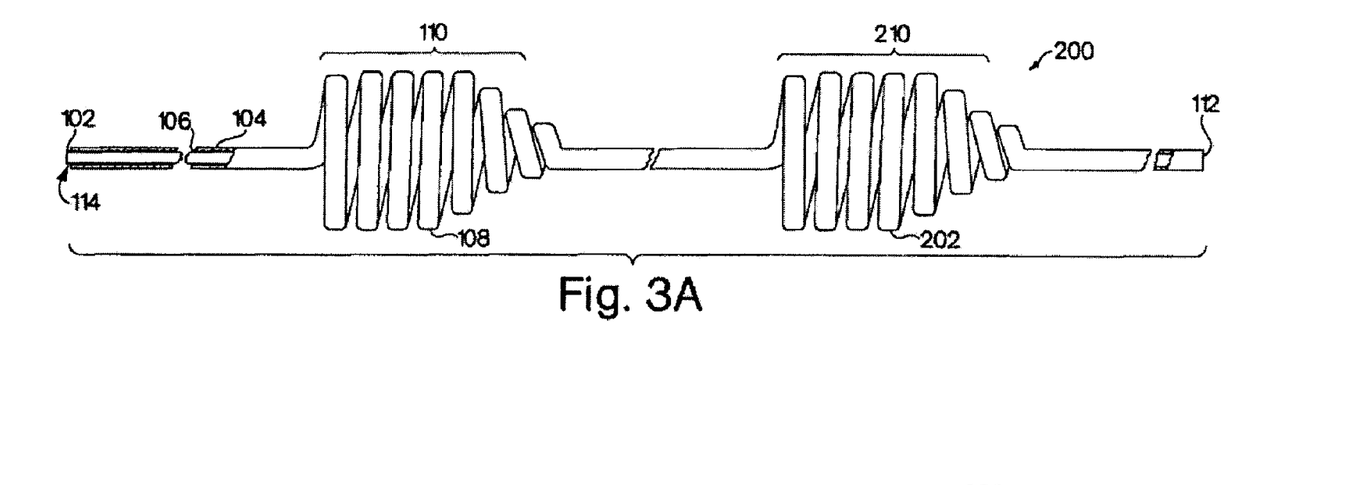
FIG. 3A is a partially sectioned schematic view of another embodiment of a medical device in accordance with the invention.

FIG. 3A is a depiction of another medical device 200 in accordance with the invention. The sleeve 104 can include a plurality of coiled configurations, for example, a first plurality of coils 108 and a second plurality of coils 202. In one embodiment, the second plurality of coils 202 is located distally to the first plurality of coils 108 and formed in a portion 210 of the sleeve 104. Each plurality of coils could form a variety of shapes, such as conical, spherical, helical, frusto-conical or combinations thereof. As discussed above with respect to the first plurality of coils 108, the second plurality of coils 202 also forms a shape when the core 102 is removed from a section of the lumen 106 extending through the second plurality of coils 202 and assumes a substantially linear configuration 210 when the core 102 is extended through the section of the lumen 106 that extends through the second plurality of coils 202.

Figure 3B:
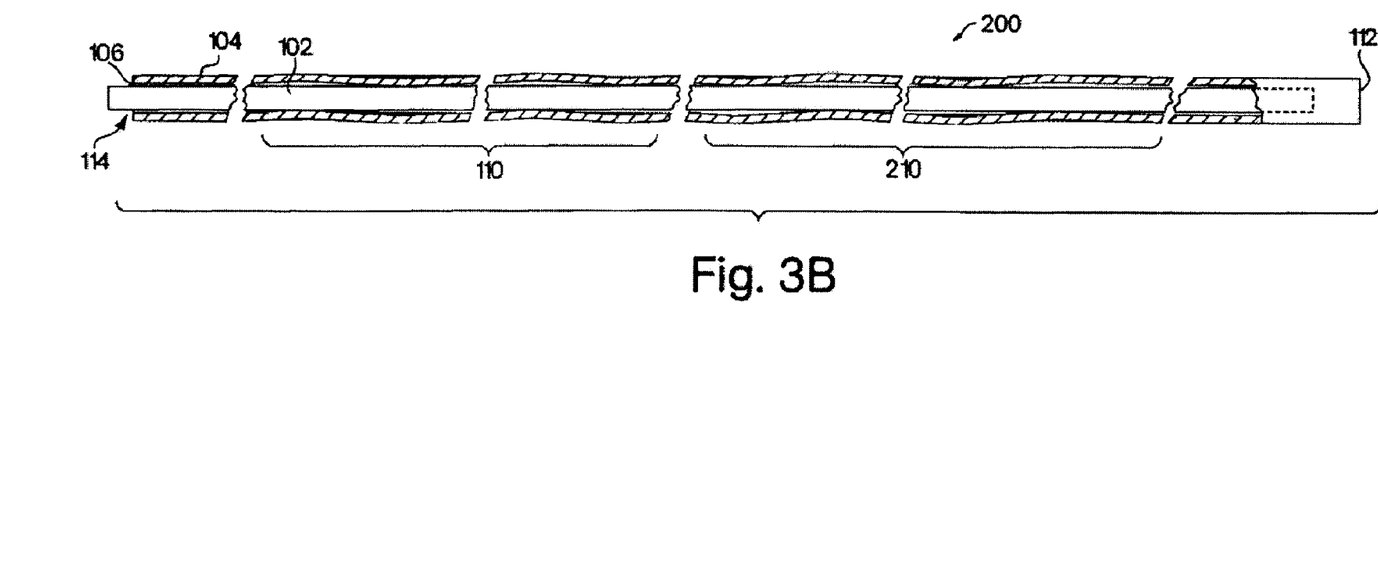
FIG. 3B is cross-sectional schematic view of the medical device of FIG. 3A, with a sleeve in a substantially linear configuration.

FIG. 3B depicts the sleeve 104 in a substantially linear configuration, where the core 102 has been extended through the section of the lumen 106 that extends through the plurality of coils 108 and the section of the lumen 106 that extends through the second plurality of coils 202. A device including two separate pluralities of coils is especially useful for the removal of two separate obstructions lodged within an anatomical lumen at the same time. A health care practitioner can insert the medical device inside a patient in a substantially linear configuration, shown in FIG. 3B, with the distal end 112 of the medical device beyond an obstruction distal to an obstruction proximal to the distal end 112 of the medical device. The health care practitioner can subsequently withdraw the core 102 from the lumen 106 of the sleeve, resulting first in the deployment of the second plurality of coils 202 encasing the distal obstruction followed by the deployment of the first plurality of coils 108 that would capture the proximal obstruction. This way, the health care practitioner uses the medical device 200 to sweep both obstructions out of the patient's body, without having to redeploy the device.

Figure 4A:
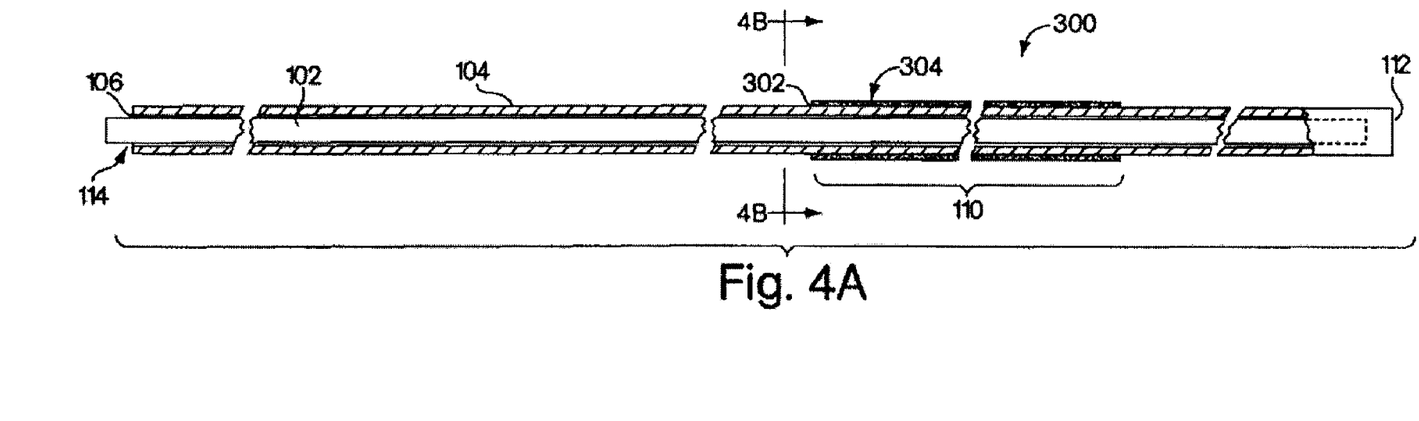
FIG. 4A is a cross-sectional schematic view of yet another embodiment of a medical device in accordance with of the invention.

FIG. 4A is another medical device 300 in accordance with the invention, where an external surface 302 of the sleeve 104 is covered by a polymeric material or sheath 304. The polymeric material 304 can be spray coated onto the external surface 302 of the sleeve 104. Alternatively, a polymer sheath 304 can be heat-shrunk onto the external surface 302 of the sleeve 104. The polymeric sheath 304 can cover the entire length of the sleeve 104 or only a portion or portions of the sleeve 104, such as the portions including the plurality of coils 108 and/or the coiled element 202 (110 and 210 respectively). The coiled element 202 can be covered by the same polymeric sheath 304 as the plurality of coils 108 or the coiled element 202 can be covered by a different polymeric sheath 304. The coiled element 202 can also be covered with a polymeric sheath 304 that has a different color or other different properties than that of the polymeric sheath 304 that covers the plurality of coils 108.

The polymeric sheath 304 can reduce the amount of friction between the turns of the plurality of coils 108 and an inner lining of an anatomical lumen or a catheter used for delivering the medical device 300, thereby decreasing the risk of damage to the surrounding area. The polymeric sheath 304 can be made of silicone, a flouroploymer, such as polytetraflouroethylene (PTFE), expanded polytetraflouroethylene (ePTFE), ethylene-tetrafluoroethylene (ETFE), or other suitable materials that exhibit laser resistant characteristics, e.g., a light color, that prevent or minimize damage to the sleeve 104 or other elements of the medical device 300 during a lithotripsy procedure.

In one embodiment, the color of the polymeric sheath 304 surrounding the plurality of coils 108 differs from the color of other portions of the polymeric sheath 304 and/or from the color of other elements of the medical device 300 in order to assist a health care practitioner in determining the location of the plurality of coils 108 within the anatomical lumen during a lithotripsy procedure. In another embodiment, the polymeric sheath 304 preferably comprises a plurality of colors along a length of the sleeve 104 to assist the health care practitioner who is performing the lithotripsy procedure to detect movement in the sleeve 104 and to gauge distances. This enables the health care practitioner to track and maneuver the sleeve 104 during various phases of the lithotripsy procedure. In one embodiment, the polymeric sheath 304 exhibits the standard color of a PTFE heat shrunk extrusion with a colored stripe along the length of the sleeve 104. As the medical device 300 is manipulated, the relative size and distances of the wound sections of the plurality of coils 108 can be readily determined by examining the spiral configuration of the colored stripe, which appears about the wound section of the plurality of coils 108. The stripe color is also preferably selected to be resistant to and reflect laser energy so as to minimize damage to the polymeric sheath 304.

In another embodiment, the sleeve 104 can be covered with a radio-opaque material that enables a health care practitioner to track the medical device 300 inside a patient under an X-ray machine. In another embodiment, the plurality of coils 108 are covered with a radio-opaque material, which enables a health care practitioner to track and maneuver the configuration of the sleeve 104 from a coiled configuration to a substantially linear configuration, as and when needed during a lithotripsy procedure.

Figure 4B:
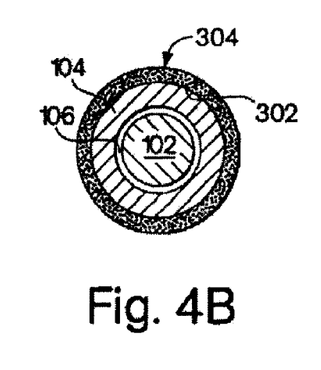
FIG. 4B is a cross-sectional schematic view of the medical device of FIG. 4A taken at line 4B-4B.

FIG. 4B is a cross-sectional view of the medical device 300 shown in FIG. 4A. In one embodiment, the medical device 300 has a generally circular cross-section with a core 102 disposed in the lumen 106 of the sleeve 104 and a polymeric coating 304 on the external surface 302 of the sleeve 104. In various embodiments, the medical device 300 can have a cross-section, such as polygonal, arcuate, or combinations of arcuate and polygonal elements.

Figure 5A:
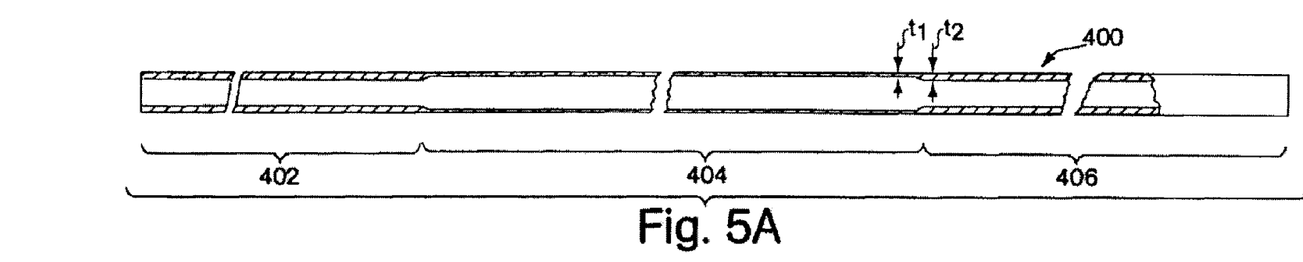
FIG. 5A is a cross-sectional schematic view of an elongate sleeve for use with an embodiment of a medical device in accordance with the invention.

FIG. 5A depicts a sleeve 104 for use with a medical device in accordance with the invention. The sleeve 104 includes at least one flexible portion 404 and one or more rigid portions 402, 406. In the embodiment shown in FIG. 5A, the sleeve 104 includes a rigid portion 402, 406 on each side of the flexible portion 404. The flexibility and rigidity in different portions of the sleeve 104 can result either from the flexible portion 404 and more rigid portions 402, 406 having different wall thicknesses ($t_1$, $t_2$) or they can be made from different materials that make portions of the sleeve flexible or more rigid. In one embodiment, the flexible portion 404 can be an expandable balloon. In the embodiment depicted in FIG. 5A, the wall of the flexible portion 404 has a thickness ($t_1$) substantially less than the thickness ($t_2$) of the walls of the rigid portions 402, 406 of the sleeve 104. The flexible portion 404 of the sleeve 104 changes form from an unexpanded state, i.e., the initial diameter of the sleeve, to an expanded state, i.e., a state of increased diameter. Alternatively, the flexible portion 404 can be sufficiently pliable to conform to the actual coil shape.

Figure 5B:
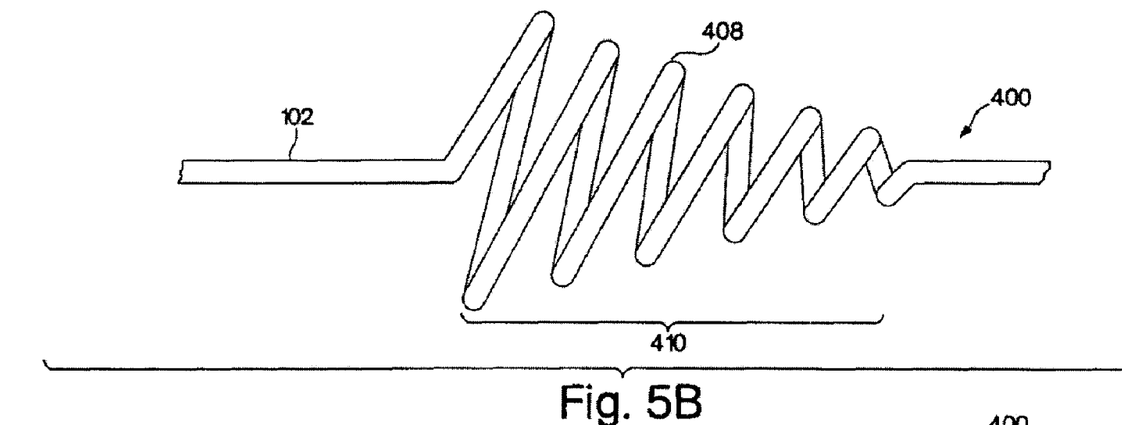
FIG. 5B is a schematic view of an elongate core for use with an embodiment of a medical device in accordance with the invention.

FIG. 5B depicts a core 102 for use with a medical device in accordance with the invention. The core 102 includes a section that is flexible, referred to as a shape-changing section 410, and is adapted to change shape when extended through the lumen 106 of the sleeve 104. In one embodiment, the shape-changing section 410 of the core 102 has a coiled configuration 408 when unrestrained. The shape-changing section 410 of the core 102 can retain a substantially linear configuration when inserted within the lumen 106 of the sleeve 104. The coiled configuration 408 of the core can include one coil or a plurality of coils resulting in a shape, such as pigtail, conical, spherical, helical, frusto-conical, or combinations thereof.

Figure 5C:
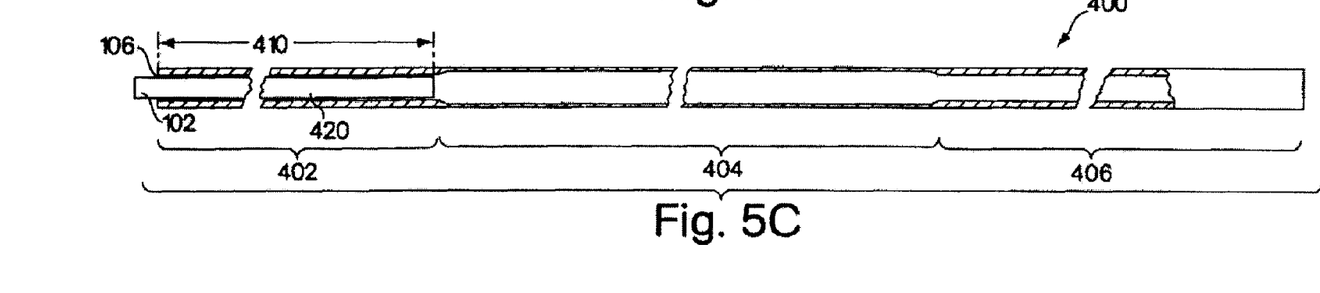
FIG. 5C is a cross-sectional schematic view of a medical device including the elongate sleeve of FIG. 5A and the elongate core of FIG. 5B.

The core 102 and the sleeve 104 can be made from the same material or different materials. In one embodiment, the core includes a shape-memory material. In another embodiment, the sleeve includes a shape-memory material. The shape-changing section 410 of the core 102 is made from a shape-memory material, which enables reversible change in the shape-changing section 410 from a coiled configuration 408 to a substantially linear configuration 420 (FIG. 5C). The flexible portion 404 of the sleeve can also be made of a shape-memory material that enables the outer diameter of the flexible portion 404 to expand when the shape-changing section 410 of the core 102 reaches the flexible portion 404 and forms the coiled configuration 408.

FIG. 5C depicts a medical device 400 including the elongate sleeve 104 of FIG. 5A and the elongate core 102 of FIG. 5B. The core 102 is inserted into the lumen 106 of the sleeve 104 such that the shape-changing section 410 of the core 102 is retained in the substantially linear configuration 420 within the rigid portion 402 of the sleeve 104.

Figure 5D:
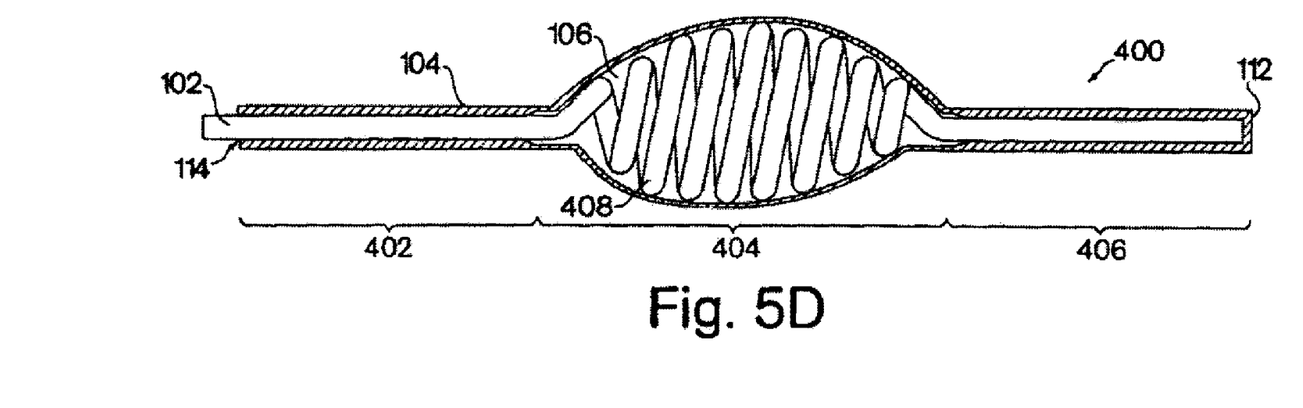
FIG. 5D is a partially sectioned schematic view of the medical device of FIG. 5C in one possible deployed configuration.

In the embodiment shown in FIG. 5D, the shape-changing section 410 of the core 102 forms a coiled configuration 408 when the shape-changing section 410 of the core reaches the flexible portion 404 of the sleeve 104. The outer diameter of the flexible portion 404 of the sleeve increases to accommodate the coiled configuration 408 of the core 102. The more rigid portions of the sleeve 402, 406 retain the other portions of the core 102 in a substantially linear configuration. Therefore, the reversible transformation of the shape-changing section 410 enables the core 102 to assume a coiled configuration 408 when the shape-changing section 410 parallels the flexible portion 404 and to be retained in the substantially linear configuration 420 when the shape-changing section 410 of the core 102 is retracted from the flexible portion 404 of the sleeve 104 to encounter the more rigid portions 402, 406 of the sleeve 104. In this manner, the shape-changing section 410 of the core and the flexible portion 404 of the sleeve 104 can change configurations depending on whether the shape-changing section 410 of the core 102 is retracted or extended through the section of the lumen 106 that extends through the flexible portion 404 of the sleeve 104.

Figure 5E:
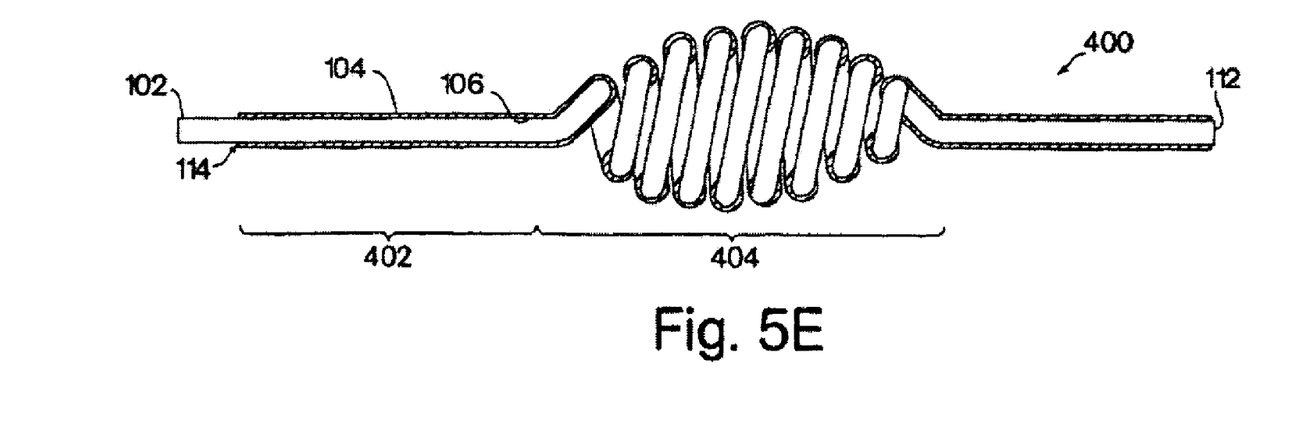
FIG. 5E is another partially sectioned schematic view of the medical device of FIG. 5C in another possible deployed configuration.

In yet another embodiment and as shown in FIG. 5E, flexible portion 404 of the sleeve 104 conforms to the shape of the shape-changing section of the core 410 when the shape-changing section of the core 410 reaches the flexible portion 404 of the sleeve. In this embodiment, the flexible portion 404 of the sleeve overlays the shape formed by the shape-changing section of the core 410, so as to adopt the identical configuration as that of the core 102. The flexible portion 404 of the sleeve 104 reverts back to a substantially linear configuration when the core 102 is retracted from within the lumen 106 of the sleeve.

A variety of conventional techniques can be used for the manufacture of the sleeve 104 including flexible and more rigid portions. In one embodiment, the flexible portion 404 and the more rigid portions 402 and 406 of the sleeve 104 can be manufactured separately and subsequently joined or sealed in an end-to-end or overlapping fashion in order to generate a single sleeve 104. The flexible and more rigid portions of the sleeve 104 can be joined by a number of means known in the art, including heat fusing, adhesive bonding, chemical bonding or mechanical attachment. In one embodiment, the flexible and more rigid portions of the sleeve are hermetically sealed. The flexible portion of the sleeve 404 can be made from a suitable polymeric material, such as ethylene vinyl acetate, which becomes more pliable upon irradiation.

Figure 6A:
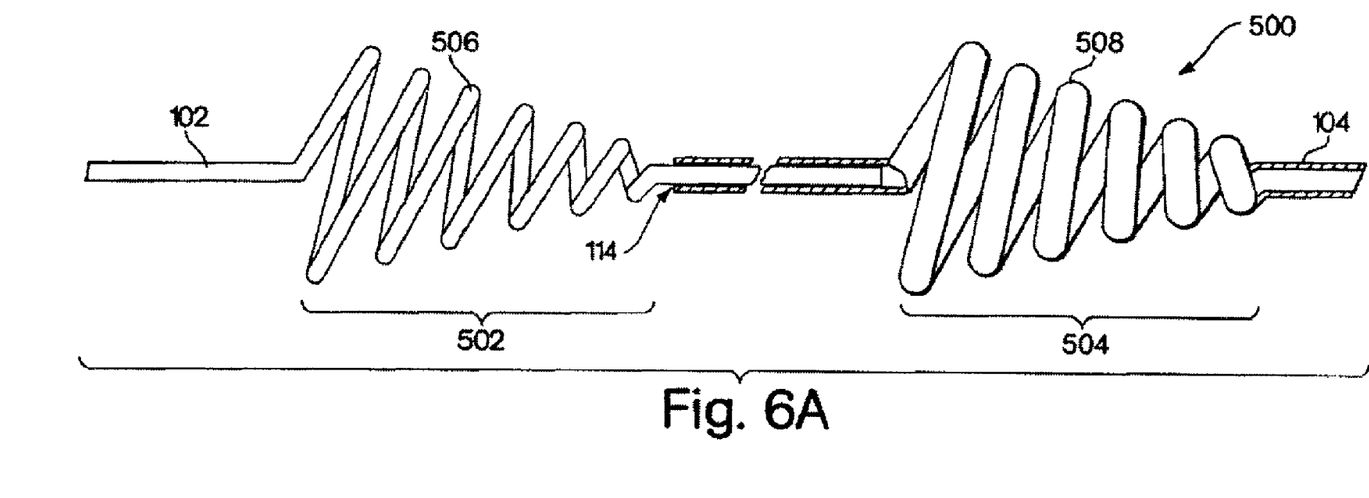
FIG. 6A is a partially sectioned schematic view of another embodiment of a medical device in accordance with the invention, wherein each of the sleeve and core sections are in a coiled configuration.
Figure 6B:
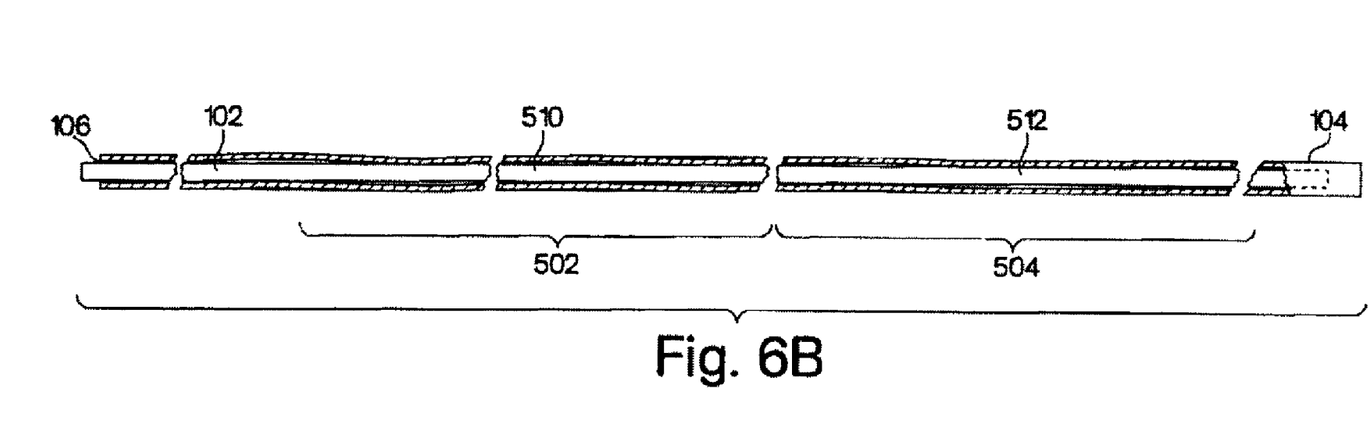
FIG. 6B is a cross-sectional schematic view of the medical device of FIG. 6A, with each of the sleeve and core sections restrained in a substantially linear configuration.
Figure 6C:
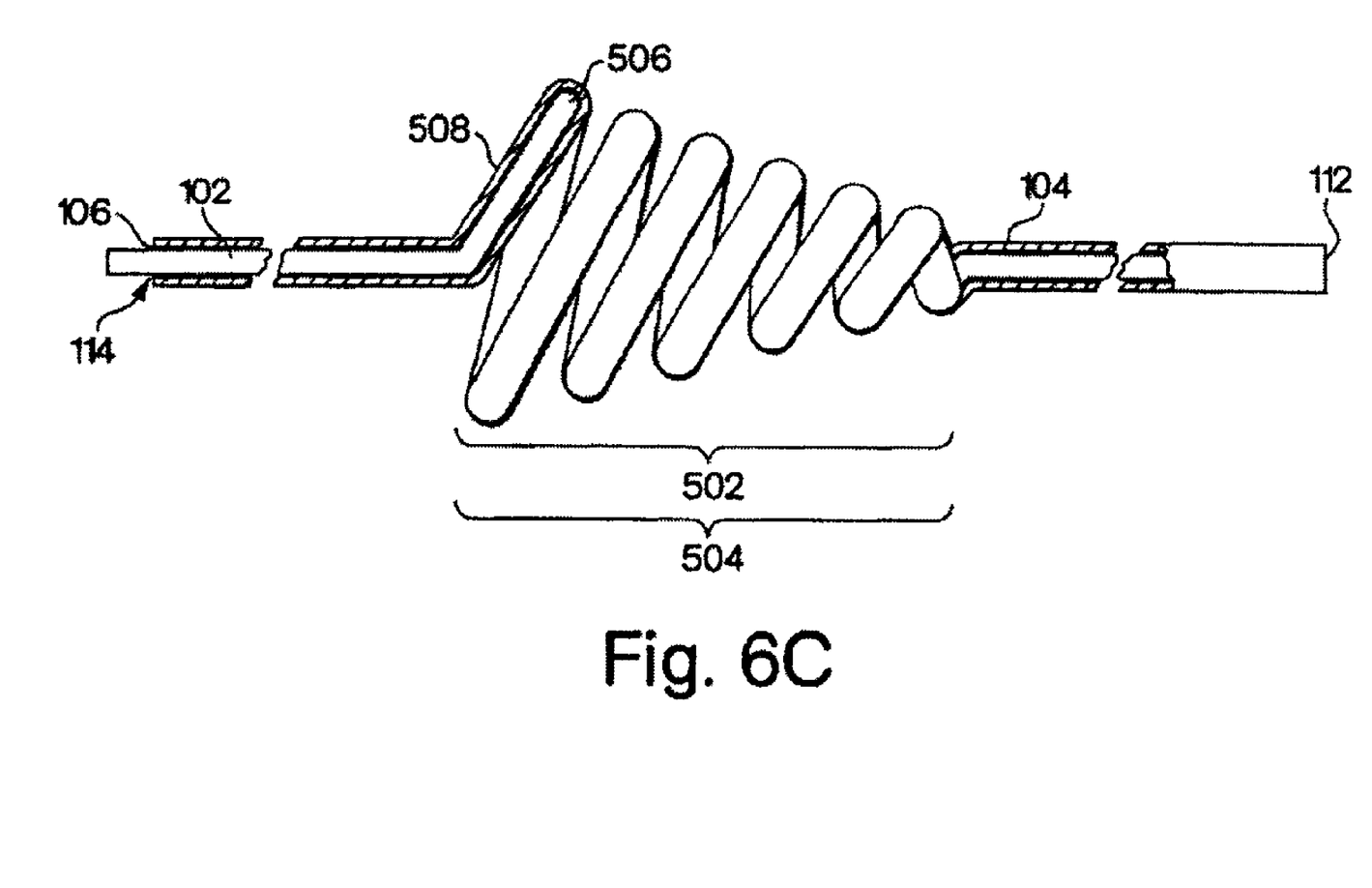
FIG. 6C is a partially sectioned schematic view of the medical device of FIG. 6A, with the sleeve and core sections in aligned and coiled configurations.

FIGS. 6A-6C are depictions of another medical device 500 in accordance with the invention, where both the core 102 and the sleeve 104 include shape-changing sections 502, 504 that can form coiled configurations 506, 508. The sleeve 104 includes a lumen 106 that extends within at least a portion of the sleeve 104 and the core 102 is slidably disposable within the lumen 106 of the sleeve 104. FIG. 6A is a depiction of the medical device 500, where the sleeve 104 and the core 102 are unrestrained, e.g., pulled apart from each other, and both shape-changing sections 502, 504 are in their coiled configurations 506, 508. In this embodiment, the core 102 is retracted from the lumen 106 of the sleeve 104.

In FIG. 6B, the shape-changing section 504 of the sleeve 104 assumes a substantially linear configuration when restrained, e.g., when a section of the core 102 other than the shape-changing section 502 is extended through a section of the lumen 106 that extends through the shape-changing section 504 of the sleeve 104. Similarly, the shape-changing section 502 of the core 102 assumes a substantially linear configuration when restrained, e.g., the core is inserted into a section of the sleeve 104 other than the shape-changing section 504.

In FIG. 6C, the shape-changing sections 502, 504 are aligned such that both assume their coiled configurations 506, 508. In one embodiment, the shape-changing sections 502, 504 can include a plurality of coils configured in a shape, such as conical, spherical, helical, frusto-conical, or combinations thereof. In one embodiment, the shape-changing sections 502, 504 are adapted to assume at least partially their coiled configurations 506, 508 when only partially aligned. Alternatively, the shape-changing sections 502, 504 can be adapted to retain their substantially linear configuration 510, 512 when only partially misaligned. In one embodiment, the coil configurations of the sleeve section and the core section are equal in size and shape. For example, the sleeve section coil configuration can include eight coils in a conical shape and the core section coil configuration can include eight coils in a complimentary conical shape.

Figure 7A:
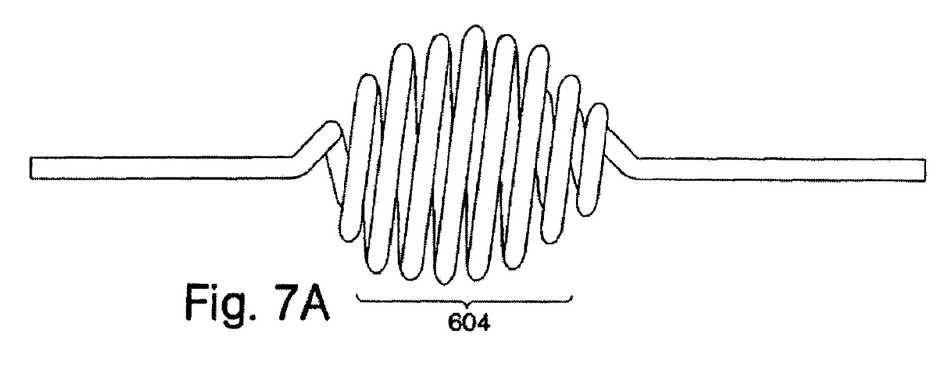
FIG. 7A is a schematic view of a spherically shaped coil configuration.
Figure 7B:
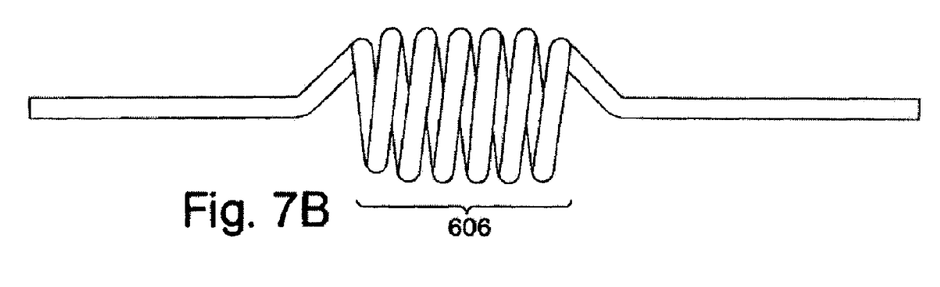
FIG. 7B is a schematic view of a helically shaped coil configuration.
Figure 7C:
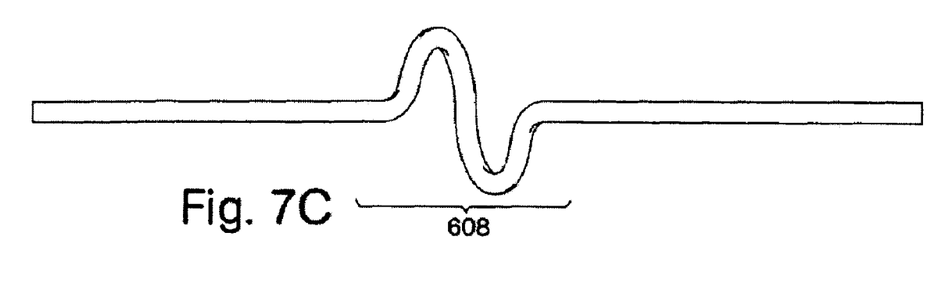
FIG. 7C is a schematic view of a pigtail shaped coil configuration.

FIGS. 7A-7C depict examples of different coil shapes that may be formed in the core 102, the sleeve 104, or both. FIG. 7A is a depiction of a spherical shape 604 formed by the plurality of coils. FIG. 7B is a depiction of a helical shape 606 formed by the plurality of coils. In FIG. 7C, the shape is a single coil in a pigtail configuration, instead of a plurality of coils, as shown in FIGS. 7A and 7B. The shape and size of the coil configuration is selected based on the intended use of the medical device.

In all the foregoing aspects of the invention, the overall length of the medical device depends on the application for which the medical device is intended. Generally, the overall length will be in the range of about 50 cm to about 250 cm. In one embodiment and with respect to urinary applications, the total length of the device 100 is about 140 cm to about 220 cm, and preferably about 200 cm. Devices for other applications, or those intended for use with children, will be different lengths.

The diameters of the sleeve 104 and the core 102 depend on the application for which the device is intended. For example, in the case of urinary applications, the maximum outside diameter of the sleeve 104 is typically in the range of about 0.5 mm to about 1.5 mm and the maximum diameter of the core 102 is such as to enable the core 102 to be slidably disposed within the lumen 106 of the sleeve 104. For other applications, for example, use of the device for the removal of an obstruction in the gastrointestinal tract, the outside diameter of the sleeve 104 can be as large as about 1 cm to about 2 cm.

In all the forgoing aspects of the medical device of the invention, the number of coils in plurality of coils of the sleeve and the core depends on the intended use of the medical device. In one embodiment, the plurality of coils has between about 5 turns and about 15 turns, and preferably about 7 turns to about 10 turns. The maximum outside diameter of the proximal end of the plurality of coils can be, for example, in the range of about 0.2 cm to about 3.0 cm, and preferably about 0.7 cm to about 0.8 cm. Adjacent turns of the plurality of coils may abut each other or be separated by small gaps 122. In the embodiment shown in FIG. 1A, the gaps 122 are up to about 2 mm wide; however, the gaps can be varied to suit a particular application.

The location of the plurality of coils also depends on the intended use of the medical device. In one embodiment, the distance 116 of the coils from the proximal end of the device is about 0.0 cm to about 15.0 cm. In another embodiment, distance 116 can be about 50 cm to about 200 cm, or about 100 cm to about 130 cm and preferably about 120 cm to about 130 cm.

In all the forgoing aspects of the medical device of the invention, the sleeve 104 and core 102 can be manufactured by, for example, injection molding or extrusion and optionally a combination of subsequent machining operations. Extrusion processes may be used to provide a uniform shape, such as a single monolithic frame. Injection molding can then be used to provide the desired geometry of the open spaces, or the open spaces could be created in the desired locations by a subsequent machining operation. In one embodiment, the sleeve 104, the core 102, or both can be made from a co-extrusion high density polyethylene for an inner portion and a polyamide for the outer portion. The co-extrusion process results in the necessary combination of flexibility, to navigate tortuous vessels, and column strength to effectively straighten out the coil. In addition, the coextrusion process can be used to produce the sleeve 104 and polymeric coating 304. Alternatively, the core 102 could be drawn wire.

In all the foregoing aspects of the invention, the shapes of the sleeve and the core can be generated by wrapping the desired portions of the sleeve or the core around a mandrel to form into the desired shape and then heating at sufficient time and temperature to set the shape into the sleeve, the core, or both. The time or the temperature largely depends on the type of material that is used for the manufacture of the sleeve and the core. Once the portions of the sleeve or the core have been heat-treated to set into the desired configurations, the sleeve or the core may be straightened by pulling at the linear portions on either side of the shape; however, the sleeve and the core will return to the wound configurations when released.

Other embodiments incorporating the concepts disclosed herein are within the spirit and scope of the invention. The described embodiments are illustrative of the invention and not restrictive.

What is claimed is:

1. A medical device comprising:
   an elongate sleeve defining a lumen extending longitudinally within at least a portion of the elongate sleeve, the sleeve comprising a first portion and a second portion more rigid than the first portion, wherein the sleeve is a unitary one-piece structure; and
   an elongate core slidably disposable within the lumen, the core including a section that changes shape when disposed in the first portion to increase an outer diameter of the sleeve, the section being retained in a substantially linear configuration when disposed in the second portion,
   wherein, when the section changes shape, the first portion of the sleeve is configured to transition from an unexpanded state to an expanded state, wherein in the unexpanded state, the first portion has a first outer diameter that is equal to an outer diameter of the second portion of the sleeve, and wherein in the expanded state, the first portion has a second outer diameter that is greater than the first outer diameter.

2. The medical device of claim 1, wherein the core comprises a shape-memory material.

3. The medical device of claim 1, wherein the sleeve comprises a shape-memory material.

4. The medical device of claim 1, wherein the first portion comprises an expandable balloon.

5. The medical device of claim 1, wherein the section that changes shape forms a coiled configuration when disposed in the first portion.

6. The medical device of claim 5, wherein the coiled configuration comprises a plurality of coils.

7. The medical device of claim 6, wherein the plurality of coils form a shape selected from the group consisting of conical, spherical, helical, frusto-conical, and combinations thereof.

8. The medical device of claim 1, wherein the first and second portions comprise walls, wherein a thickness of the first portion wall is substantially less than a thickness of the second portion wall.

9. The medical device of claim 1, wherein the first portion and the second portion comprise different materials.

10. The medical device of claim 1, wherein the sleeve includes a coating disposed on an external surface of the sleeve.

11. The medical device of claim 10, wherein the coating comprises a polymeric material.

12. The medical device of claim 11, wherein the polymeric material is selected from the group consisting of polytetraflouroethylene, expanded polytetraflouroethylene, ethylene-tetrafluoroethylene, and silicone.

13. The medical device of claim 1, wherein each of the sleeve and core has a cross-section selected from the group consisting of polygonal, arcuate, and combinations of arcuate and polygonal elements.

14. A medical device comprising:
   an elongate sleeve defining a lumen extending longitudinally within at least a portion of the elongate sleeve, the sleeve including a sleeve section that changes shape; and
   an elongate core slidably disposable within the lumen, the core including a core section that changes shape, each of the sleeve and core sections retaining a substantially linear configuration when restrained and forming a substantially coiled, configuration when aligned.

15. The medical device of claim 14, wherein the sleeve comprises a shape-memory material.

16. The medical device of claim 14, wherein the core comprises a shape-memory material.

17. The medical device of claim 14, wherein the coiled configuration comprises a plurality of coils.

18. The medical device of claim 17, wherein the plurality of coils form a shape selected from the group consisting of conical, spherical, helical, frusto-conical, and combinations thereof.

19. The medical device of claim 14; wherein each of the sleeve and core sections forms the substantially coiled configuration when partially aligned.

20. The medical device of claim 14, wherein each of the sleeve section and core section retains the substantially linear configuration when at least partially misaligned.

21. The medical device of claim 14, wherein the sleeve includes a coating disposed on an external surface of the sleeve.

22. The medical device of claim 21, wherein the coating comprises a polymeric material.

23. The medical device of claim 22, wherein the polymeric material is selected from the group consisting of polytetraflouroethylene, expanded polytetraflouroethylene, ethylene-tetrafluoroethylene, and silicone.

24. The medical device of claim 14, wherein each of the sleeve and core has a cross-section selected from the group consisting of polygonal, arcuate, and combinations of arcuate and polygonal elements.

* * * * *